United States Patent
Naya et al.

(10) Patent No.: US 8,803,105 B2
(45) Date of Patent: Aug. 12, 2014

(54) OPTICAL FIELD ENHANCEMENT DEVICE

(71) Applicant: FUJIFILM Corporation, Tokyo (JP)

(72) Inventors: Masayuki Naya, Ashigarakami-gun (JP); Shinya Hakuta, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 13/785,897

(22) Filed: Mar. 5, 2013

(65) Prior Publication Data

US 2013/0182343 A1 Jul. 18, 2013

Related U.S. Application Data

(63) Continuation of application No. PCT/JP2011/004965, filed on Sep. 5, 2011.

(30) Foreign Application Priority Data

Sep. 17, 2010 (JP) ................. 2010-208983

(51) Int. Cl.
| | |
|---|---|
| *G01N 21/68* | (2006.01) |
| *G01N 21/65* | (2006.01) |
| *G02B 17/00* | (2006.01) |
| *G01N 21/64* | (2006.01) |
| *B82Y 20/00* | (2011.01) |

(52) U.S. Cl.
CPC ............. *G02B 17/00* (2013.01); *G01N 21/658* (2013.01); *B82Y 20/00* (2013.01); *G01N 21/648* (2013.01); *Y10S 977/834* (2013.01)
USPC ........... 250/459.1; 362/337; 977/834

(58) Field of Classification Search
CPC ............ G03H 1/2294; G03H 2240/15; G03H 2222/31; G03H 2225/52; G03H 2225/22
USPC ............... 362/337, 339, 620, 626; 250/459.1
See application file for complete search history.

(56) References Cited

U.S. PATENT DOCUMENTS

| | | | |
|---|---|---|---|
| 4,190,321 | A | 2/1980 | Dorer et al. |
| 4,252,843 | A | 2/1981 | Dorer et al. |
| 5,455,178 | A | 10/1995 | Fattinger |
| 2005/0105085 | A1 | 5/2005 | Naya |
| 2006/0119853 | A1 | 6/2006 | Baumberg et al. |
| 2008/0037022 | A1 | 2/2008 | Nishikawa et al. |
| 2008/0310026 | A1 | 12/2008 | Nakayama et al. |
| 2009/0273779 | A1 | 11/2009 | Baumberg et al. |

FOREIGN PATENT DOCUMENTS

| | | |
|---|---|---|
| JP | 61-48124 A | 3/1986 |
| JP | 5-346398 A | 12/1993 |
| JP | 9-202649 A | 8/1997 |
| JP | 2005-172569 A | 6/2005 |
| JP | 2006-514286 A | 4/2006 |

(Continued)

OTHER PUBLICATIONS

Ghadarghadr et al.,"Plasmonic array nanoantennas on layered substrates: modeling and radiation characteristics", Optics Express, vol. 17, No. 21, 2009, pp. 18556-18570.

*Primary Examiner* — Jennifer L. Doak
(74) *Attorney, Agent, or Firm* — Birch, Stewart, Kolasch & Birch, LLP

(57) ABSTRACT

An optical field enhancement device which includes a transparent substrate having a transparent fine uneven structure on a surface and a metal film formed on a surface of the fine uneven structure on the surface of the substrate and allows projection of excitation light and detection of detection light either from a front surface side of the metal film or from a back surface side of the transparent substrate.

8 Claims, 6 Drawing Sheets

(56) References Cited

FOREIGN PATENT DOCUMENTS

| | | |
|---|---|---|
| JP | 2006-145230 A | 6/2006 |
| JP | 2008-519254 A | 6/2008 |
| JP | 2008-233880 A | 10/2008 |
| JP | 2008-286778 A | 11/2008 |
| JP | 4347801 B2 | 10/2009 |
| JP | 2010-66704 A | 3/2010 |
| JP | 2010-96645 A | 4/2010 |
| JP | 2010-203900 A | 9/2010 |
| WO | WO 2005/078415 A1 | 8/2005 |

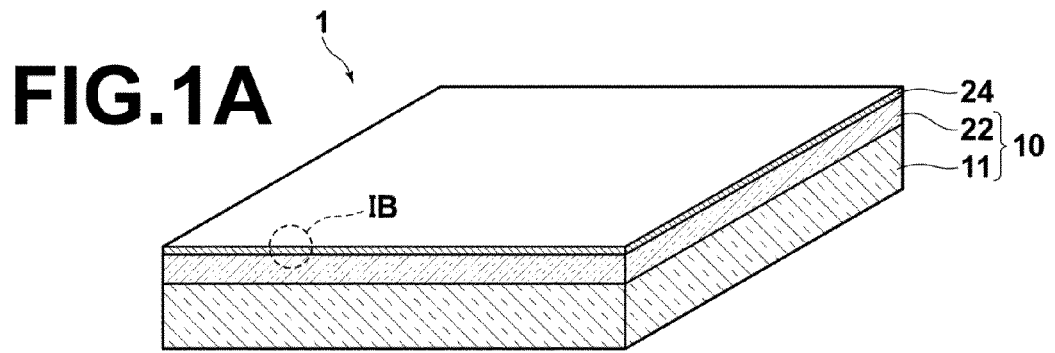
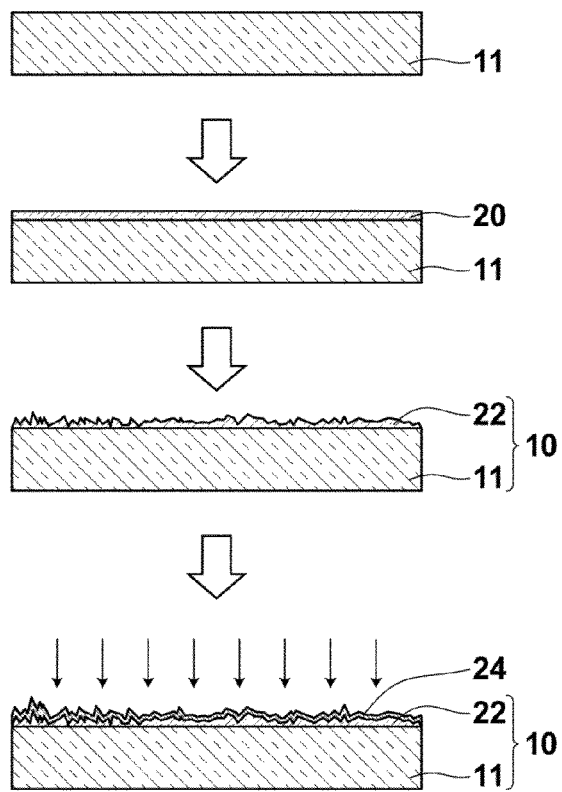

OPTICAL FIELD ENHANCEMENT DEVICE

CROSS REFERENCE TO RELATED APPLICATIONS

This non-provisional application is a Continuation of International Application No. PCT/JP2011/004965 filed on Sep. 5, 2011, which claims the benefit of Japanese Patent Application No. 2010-208983 filed in Japan on Sep. 17, 2010. The entire contents of all of the above applications are hereby incorporated by reference.

TECHNICAL FIELD

The present invention relates to an optical field enhancement device having a fine uneven metal structure capable of inducing localized plasmon.

BACKGROUND ART

Electric-field enhancement devices, such as sensor devices, Raman spectroscopy devices, and the like, that utilize an electric-field enhancement effect of a phenomenon of localized plasmon resonance on a metal surface are known. The Raman spectroscopy is a method for obtaining a Raman scattered light spectrum (Raman spectrum) by separating scattered light obtained by projecting single wavelength light onto a substance, and it is used for identifying a substance or the like.

The Raman spectroscopy includes a method called surface-enhanced Raman spectroscopy (SERS) that utilizes an optical field enhanced by localized plasmon resonance in order to enhance weak Raman scattered light as described, for example, in S. Ghadarghadr et al., "Plasmonic array nanoantennas on layered substrates: modeling and radiation characteristics", Optics Express, Vol. 17, No. 21, pp. 18556-18570, 2009. This makes use of the principle that if light is projected onto a metal body, in particular, onto a metal body having a nano-order uneven pattern on a surface with a substance being in contact with the surface, optical field enhancement occurs due to localized plasmon resonance and the intensity of Raman scattered light of the sample in contact with the surface of the metal body is enhanced. The surface-enhanced Raman spectroscopy may be implemented by using a substrate having an uneven metal structure on a surface as a carrier (substrate) for carrying a subject.

As for the substrate having a fine uneven metal structure on a surface, a substrate manufactured by forming an uneven pattern on a surface of a Si substrate and forming a metal film on the surface of the uneven pattern is mainly used as described, for example, in PCT Japanese Publication No. 2006-514286, Japanese Patent No. 4347801, and Japanese Unexamined Patent Publication No. 2006-145230.

Further, a substrate produced by anodizing a surface of an Al substrate to turn a portion into a metal oxide ($Al_2O_3$) layer and filling a metal in a plurality of fine pores spontaneously formed in the metal oxide layer during the anodizing process and opens at the surface of the metal oxide layer is also proposed as described, for example, in Japanese Unexamined Patent Publication No. 2005-172569.

DISCLOSURE OF THE INVENTION

Conventional optical field enhancement substrates disclosed in PCT Japanese Publication No. 2006-514286, Japanese Patent No. 4347801, and Japanese Unexamined Patent Publication Nos. 2006-145230 and 2005-172569 are configured such that a fine uneven structure is formed on a surface of an opaque substrate, such as Si or Al, and a metal film is formed on the surface of the fine uneven structure or a metal is embedded in the depressions. Japanese Unexamined Patent Publication No. 2005-172569 describes an example case in which a transparent substrate, such as a glass substrate, is used, but the fine uneven structure itself is made of an opaque material, such as silicon or germanium.

Conventional Raman spectroscopy apparatuses are configured such that Raman scattered light is detected from the front surface side of a sample. In the case where a sample having a size in the order of micrometers or greater is used as the subject, however, the sample itself acts as a blocking body against the Raman scattered light, whereby it has been difficult to receive weak Raman scattered light with a high signal-to-noise ratio.

The present invention has been developed in view of the circumstances described above, and it is an object of the present invention to provide an optical field enhancement device capable of detecting Raman scattered light with improved sensitivity.

An optical field enhancement device of the present invention is a device, including a transparent substrate having a transparent fine uneven structure on a surface and a metal film formed on a surface of the fine uneven structure on the surface of the substrate, wherein the device is configured such that an enhanced optical field is created on a surface of the metal film by an electric-field enhancement effect of localized plasmon induced on the surface of the metal film by light projected onto the fine uneven structure on which the metal film is formed.

Here, the metal film is formed on the surface of the fine uneven structure and the surface of the metal film has a fine uneven structure formed according to the transparent uneven structure. The fine uneven structure on the surface of the metal film may be anything as long as it is capable of generating localized plasmon by receiving light. Generally, the fine uneven structure capable of generating localized plasmon is an uneven structure having an average size and an average pitch of protrusions and depressions constituting the uneven structure smaller than the wavelength of the light.

Preferably, the average pitch of the protrusions and depressions and the distance (depth) between the top of a protrusion and the bottom of a depression are not greater than 200 nm.

The average pitch of the protrusions and depressions is obtained by imaging the surface of the fine uneven structure with a SEM (Scanning Electron Microscope), then digitizing the image through image processing, and performing a statistical procedure.

The average depth of the protrusions and depressions is obtained by measuring the surface shape with an AFM (Atom Force Microscope) and performing a statistical procedure.

The term "transparent" as used herein refers to having a transmittance of 50% or greater for the light projected onto the fine uneven structure and light generated from the subject by the projected light. Preferably, the transmittance for these light beams is not less than 75% and more preferably, not less than 90%.

In the optical field enhancement device of the present invention, the transparent substrate may be formed of a transparent substrate body and a fine uneven structure layer provided on a surface of the transparent substrate body, wherein the layer is made of a material different from that of the transparent substrate body and constitutes the fine uneven structure.

In particular, the fine uneven structure layer may preferably be made of boehmite.

The metal film may be any film made of a metal that generates localized plasmon by receiving the light described above, but at least one type of metal selected from the group consisting of Au, Ag, Cu, Al, Pt, and alloys based on these metals is preferable. Among them, Au and Ag are particularly preferable.

Preferably, the metal film has a thickness of 10 to 100 nm.

The optical field enhancement device of the present invention may include a transparent second fine uneven structure acting as an antireflection film on a back surface of the transparent substrate.

Here, it is preferable that the second fine uneven structure is formed of a fine uneven structure layer made of boehmite.

The optical field enhancement device of the present invention may be formed into a sample cell having a liquid sample holding member for holding a liquid sample on the metal film of the transparent substrate.

Further, the optical field enhancement device of the present invention may be formed into a sample flow cell, wherein the liquid sample holding member has an inlet section and an outlet section for a liquid.

The optical field enhancement device of the present invention includes a transparent substrate having a transparent fine uneven structure on a surface and a metal film formed on a surface of the fine uneven structure on the surface of the substrate. That is, the metal film is provided on the transparent fine uneven structure and the metal film itself is formed in an uneven pattern. If light is projected onto the metal film, therefore, localized plasmon may be effectively induced on the surface of the metal film and an optical field enhancement effect may be obtained by the localized plasmon. In the case where a subject is placed on the optical field enhancement device and light is projected onto an area of the device on which the subject is placed, light generated from the subject is enhanced by the optical field enhancement effect, whereby the light may be detected with high sensitivity.

The optical field enhancement device of the present invention, in particular, uses a transparent substrate, so that the light (excitation light) may be projected onto the substrate either from the front surface side of the metal film or from the back surface side of the transparent substrate. Likewise, the light (detection light) generated from the subject can be detected either from the front surface side of the metal film or from the back surface side of the transparent substrate. The selection as to from which side, the front surface side of the metal film or back surface side of the transparent substrate, excitation light is to be projected or detection light is to be detected may be made freely according to the type, size, and the like of the subject in order to perform high sensitivity detection. That is, the use of the optical field enhancement device of the present invention allows a high degree of flexibility in measurement and detection with an improved signal-to-noise ratio.

In the optical field enhancement device of the present invention, if a configuration is adopted in which the transparent substrate is formed of a transparent substrate body and a fine uneven structure layer provided on a surface of the transparent substrate body, the layer being made of a material different from that of the transparent substrate body and constituting the fine uneven structure, and if the fine uneven structure layer is made of boehmite, a fine uneven structure having high in-plane uniformity may be manufactured by very simple manufacturing method and the manufacturing cost may be reduced significantly in comparison with that of a conventional device.

BRIEF DESCRIPTION OF DRAWINGS

FIG. 1A is a perspective view of an optical field enhancement substrate 1 according to a first embodiment of the optical field enhancement device of the present invention.

FIG. 1B is an enlarged view of a portion TB of a side face of the optical field enhancement substrate 1 shown in FIG. 1A.

FIG. 2 shows a manufacturing method of an optical field enhancement substrate, illustrating a cross-section of the substrate at each step of the method.

BEST MODE FOR CARRYING OUT THE INVENTION

Figure 3:
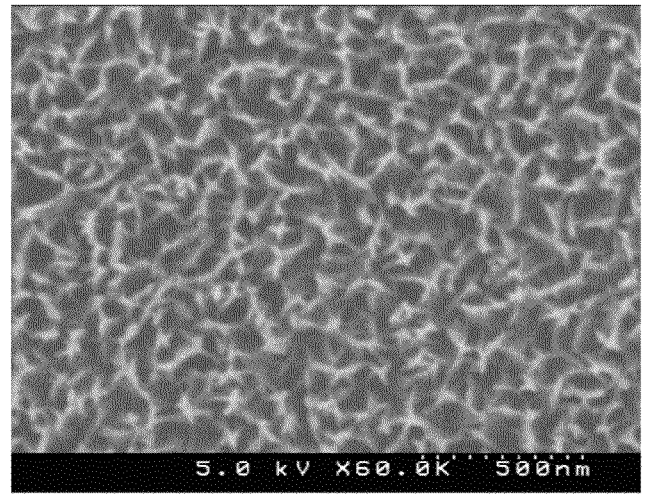
FIG. 3 is a SEM image of a boehmite layer surface.

Hereinafter, embodiments of the optical field enhancement device of the present invention will be described with reference to the accompanying drawings. Each component in the drawings is not necessarily drawn to scale for ease of visual recognition.

First Embodiment

FIG. 1A is a perspective view of an optical field enhancement substrate 1 according to a first embodiment of the optical field enhancement device of the present invention, and FIG. 13 is an enlarged view of a portion 1B of a side face of the optical field enhancement substrate 1 shown in FIG. 1A.

As illustrated in FIGS. 1A, 1B, the optical field enhancement substrate 1 includes a transparent substrate 10 having a fine uneven structure 22 on a surface and a metal film 24 formed on a surface of the fine uneven structure 22. The metal film 24 is formed along the fine uneven structure 22 such that a fine metal uneven structure is formed. Thus, the optical field enhancement substrate 1 includes a fine uneven metal structure on a surface and may function as an optical field enhancement device capable of obtaining an optical field enhancement effect of localized plasmon resonance.

The optical field enhancement substrate 1 is configured such that localized plasmon resonance is induced by light (excitation light) projected onto the fine uneven structure 22 on which the metal film 24 is formed (fine uneven metal structure), and enhanced optical field is created on the surface of the metal film 24 by the localized plasmon resonance.

The fine uneven structure 22 is an uneven structure of a size that causes the average size and pitch of protrusions of uneven pattern on the fine metal structure provided by forming the metal film 24 on the fine uneven structure 22 to become smaller than the wavelength of the excitation light, but the fine uneven structure 22 may be anything as long as it is capable of generating localized plasmon. In particular, it is preferable that the fine uneven structure 22 has an average depth of not greater than 200 nm from the top of a protrusion to the bottom of an adjacent depression and an average pitch of not greater than 200 nm between the tops of the most adjacent protrusions across a depression.

In the present embodiment, the transparent substrate 10 is formed of a transparent substrate body 11 made of glass or the like and a boehmite layer made of a material different from that of the body 11 and constitutes the fine uneven structure 22 (hereinafter, referred to as "boehmite layer 22" or "fine uneven structure layer 22").

The metal film 24 may be a film made of any metal as long as it is capable of generating localized plasmon by receiving excitation light but, for example, a film made of at least one type of metal selected from the group consisting of Au, Ag, Cu, Al, Pt and alloys based on these metals is preferable. Among them, Au and Ag are particularly preferable.

There is not any specific restriction on the film thickness of the metal film 24 as long as it allows an uneven pattern to be maintained that can generate localized plasmon by receiving excitation light as a fine uneven metal structure when formed on the fine uneven structure layer 22, but the preferable film thickness range is from 10 to 100 nm.

In the embodiment described above, the fine uneven structure layer 22 of the transparent substrate 10 is made of boehmite, but the layer may be made of any transparent material other than the boehmite. For example, the transparent substrate 10 may also be formed by performing an anodization process on an aluminum substrate to produce an anodized alumina having multiple fine pores in an upper layer of the aluminum substrate, removing the unanodized aluminum portion to obtain an anodized alumina layer as the fine uneven structure layer 22, and fixing the fine uneven structure layer 22 on the transparent substrate body 11 made of glass or the like.

The fine uneven structure is not limited to the structure made of a material different from that of the transparent substrate body and it may be made of the same material as that of the substrate body by processing the surface of the transparent substrate body. For example, a glass substrate having a fine uneven structure on a surface formed through lithography and dry-etching may be used as the transparent substrate.

The fine uneven structure 22 is most preferably made of boehmite as it is formed by an easy method.

A method of manufacturing the optical field enhancement substrate 1 according to the present embodiment will now be described with reference to FIG. 2.

A plate-like transparent substrate body 11 is provided. Then, the transparent substrate body 11 is cleaned with pure water. Thereafter, aluminum 20 is formed on the transparent substrate body 11 with a thickness of about several tens of nanometers by sputtering. Then, the transparent substrate body 11 with the aluminum 20 is immersed in boiling pure water and taken out after several minutes (about five minutes). This boil treatment (boehmite treatment) turns the aluminum 20 into the transparent boehmite layer 22 constituting a fine uneven structure. Then, a metal film 24 is formed on the boehmite layer 22. In this way, the optical field enhancement substrate 1 is created.

FIG. 3 is a SEM image obtained by imaging, using a SEM (Hitachi, S4100), the surface of a boehmite layer provided on a transparent substrate body (BK-7, Corning Eagle 2000) by sputtering aluminum on the transparent substrate body with a thickness of 50 nm and boil treating the substrate body with the sputtered aluminum for five minutes. In FIG. 3, portions appearing whitish correspond to protrusions and portions appearing grayish correspond to depressions. Although, the uneven pattern is irregular, the pattern is uniformly formed over the entire surface and the fine uneven structure has high in-plane uniformity.

Second Embodiment

Figure 4A:
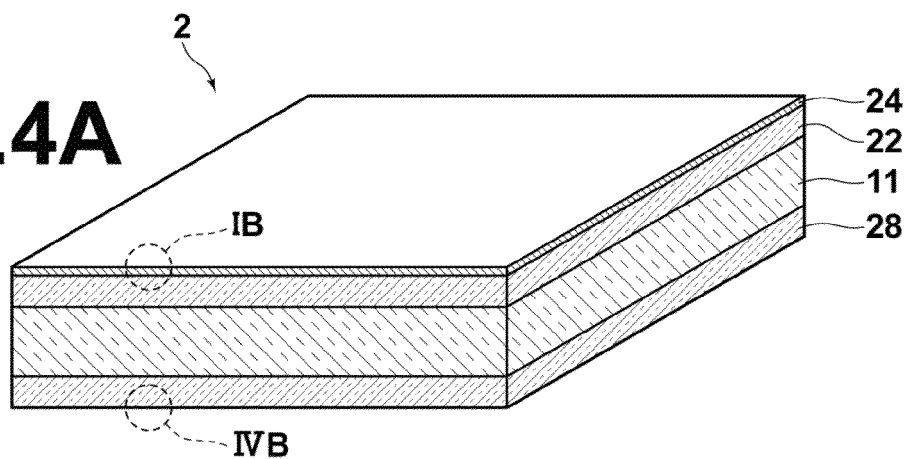
FIG. 4A is a perspective view of an optical field enhancement substrate 2 according to a second embodiment of the optical field enhancement device.
Figure 4B:
FIG. 4B is an enlarged view of a lower portion IVB of a side face of the optical field enhancement substrate 2 shown in FIG. 4A.

Next, an optical field enhancement substrate according to a second embodiment of the optical field enhancement device of the present invention will be described. FIG. 4A is a perspective view of an optical field enhancement substrate 2 of the present embodiment, and FIG. 4B is an enlarged view of a lower portion IVB of a side face of the optical field enhancement substrate 2 shown in FIG. 4A.

The optical field enhancement substrate 2 is a substrate provided by adding a second fine uneven structure layer 28 to the back surface of the optical field enhancement substrate 1 of the first embodiment.

The second fine uneven structure layer 28 is identical to the first fine uneven structure layer 22 provided on the front surface of the transparent substrate 10 and may be made of a boehmite layer. The fine uneven structure layer 28 provided on the back surface functions as an antireflection film when light is projected.

The optical field enhancement substrate 2 may be obtained by forming aluminum on the back surface of the transparent substrate as well as on the front surface in the method of manufacturing the optical field enhancement substrate 1 of the first embodiment and performing a boil treatment after that. The aluminum on the front and back surfaces of the substrate turns into boehmite through boil treatment in pure water and the optical field enhancement substrate 2 may have similar fine uneven structures 22, 28 on the front and back surfaces respectively.

Figure 5:
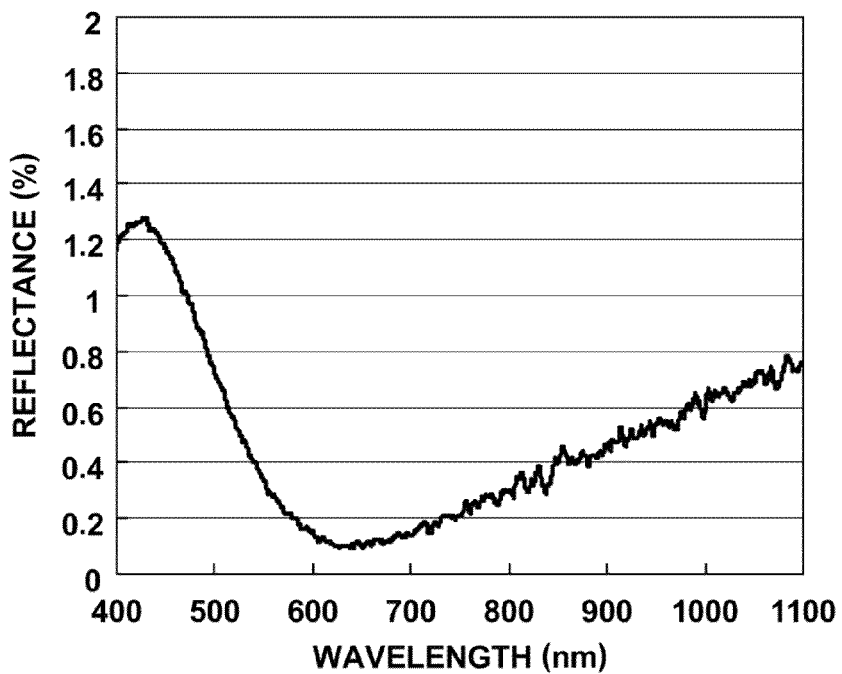
FIG. 5 illustrates wavelength dependency of light reflection of a boehmite layer.

FIG. 5 illustrates a light reflection curve of a substrate with a boehmite layer formed by sputtering aluminum on a transparent substrate body (BK-7, Coring, Eagle 2000) with a thickness of 50 nm and boil treating the substrate body with the boehmite layer for five minutes when light is inputted from the front surface side of the boehmite layer at right angle with respect to the surface. In the illustrated example, a reflectance of about 0.1% is achieved with respect to a wavelength close to 650 nm. The wavelength where the reflectance becomes minimal can be adjusted, for example, by changing the thickness of aluminum formed first by sputtering and controlling interference.

Third Embodiment

Figure 6A:
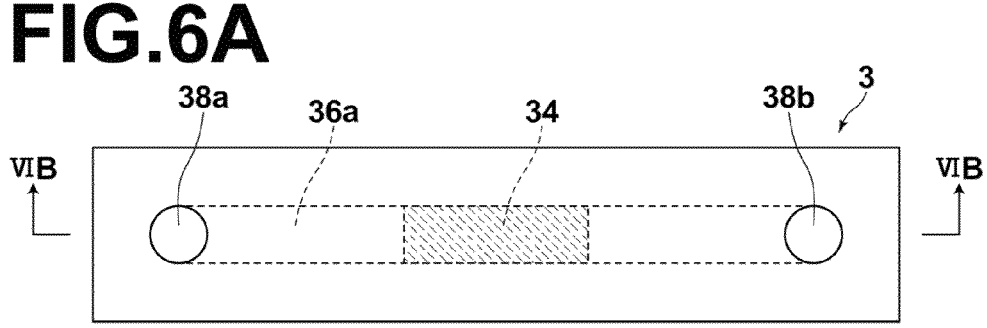
FIG. 6A is a plan view of an optical field enhancement sample cell 3 according to a third embodiment of the optical field enhancement device.
Figure 6B:
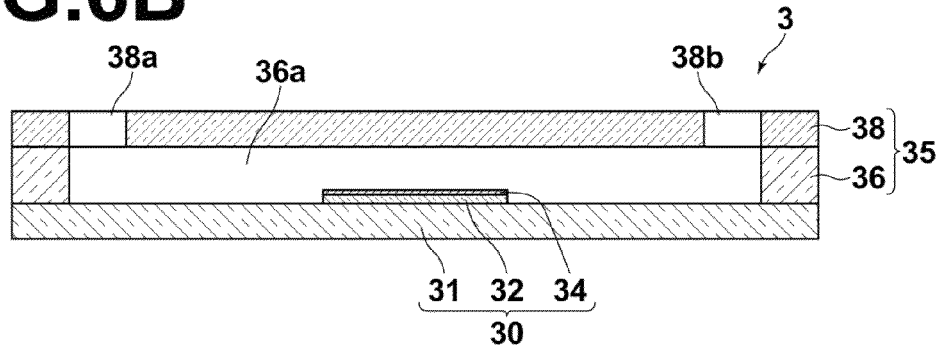
FIG. 6B is a cross-sectional view of the optical field enhancement sample cell 3 shown in FIG. 6A taken along the line VIB-VIB.

A sample cell according to a third embodiment of the optical field enhancement device of the present invention will be described. FIG. 6A is a plan view of an optical field enhancement sample cell 3 according to a third embodiment and FIG. 6B is a cross-sectional view of the optical field enhancement sample cell 3 taken along the line VIB-VIB in FIG. 6A.

The optical field enhancement sample cell 3 of the present embodiment includes: an optical field enhancement substrate 30 having a transparent substrate body 31, a transparent fine uneven structure 32 provided on the surface of the body, and metal film 34 provided on the fine uneven structure 32; and a liquid sample holding member 35 for holding a liquid sample provided on the metal film 34.

The structure of the optical field enhancement substrate 30 is substantially identical to that of the optical field enhancement substrate 1 of the first embodiment. That is, the fine uneven structure 32 and the metal film 34 are identical to the fine uneven structure 22 and the metal film 24 of the first optical field enhancement device 1 shown in FIG. 1B, and their constituent materials and forming methods are also identical.

For example, the liquid sample holding member 35 may be formed of a spacer 36 for holding a liquid sample on the metal film 34 and forming a flow path 36a and a transparent upper plate 38, such as a glass plate, having an injection port (inlet) 38a for injecting a liquid sample and a discharge port (outlet) 38b for discharging the liquid sample flowed down the flow path 36a.

The optical field enhancement sample cell 3 of the present embodiment may be obtained by manufacturing the optical field enhancement substrate 30 by a method identical to that of the substrate 1 of the first embodiment and bonding the spacer 36 and the upper plate to the substrate 30.

Note that the spacer 36 and the upper plate 38 may be formed integrally. Alternatively, the spacer 36 may be formed integrally with the transparent substrate body 31.

In the aforementioned embodiment, the description has been made of a case in which an optical field enhancement device of a type of a flow-path-like sample cell (flow cell) having an inlet and an outlet. But it may be configured as an optical field enhancement sample cell only for holding a liquid sample on the metal film instead of a cell capable of flowing in and out a liquid.

Further, a second transparent fine uneven structure layer that functions as an antireflection film may be provided on an area of the back surface of the optical field enhancement substrate 30 corresponding to the area of the metal film 34, as in the optical field enhancement substrate 2 of the second embodiment.

The optical field enhancement device of the present invention described in each aforementioned embodiment may be used preferably in a measurement method and apparatus in which a subject is placed on the fine uneven metal structure of the device, then excitation light is projected onto the area of the structure on which the subject is placed, and light emitted from the subject by the projection of the excitation light is detected. For example, the device can be applied to enhanced Raman spectroscopy, fluorescence detection, and the like. That is, the device may be used as a Raman enhancing device in enhanced Raman spectroscopy and a fluorescence enhancing device in fluorescence detection. Further, the use of the optical field enhancement device of the present invention in detecting not only the Raman scattered light, fluorescence but also Rayleigh scattered light, Mie scattered light, or second harmonics generated from a subject that has received excitation light allows enhanced light to be detected due to enhanced optical field associated with localized plasmon resonance.

(Raman Spectroscopy and Raman Spectroscopy Apparatus)

As an example of measurement method using the aforementioned optical field enhancement substrate 1, a Raman spectroscopy and a Raman spectroscopy apparatus will now be described.

Figure 7:
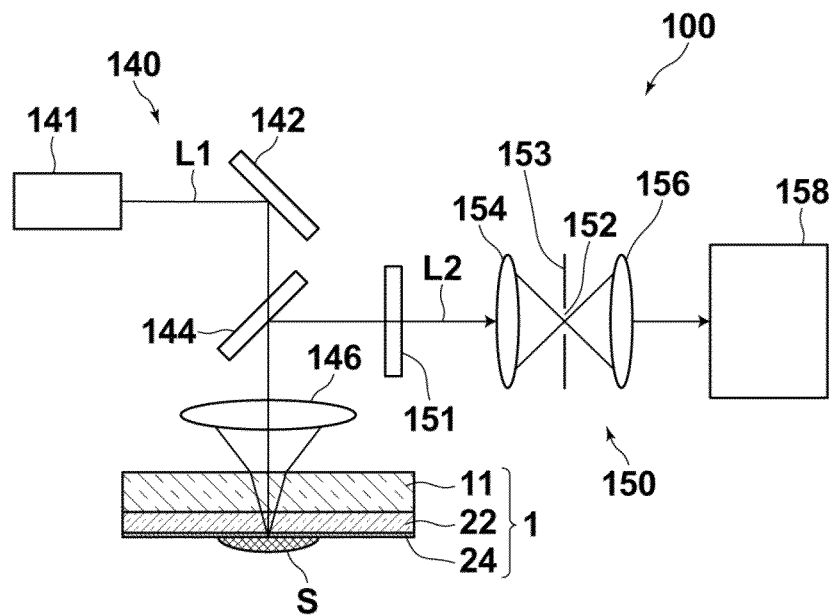
FIG. 7 is a schematic diagram of an enhanced Raman spectroscopy apparatus having the optical field enhancement substrate 1, illustrating the configuration thereof.

FIG. 7 is a schematic diagram of the Raman spectroscopy apparatus having the optical field enhancement substrate 1 according to the first embodiment described above, illustrating the configuration thereof.

As illustrated in FIG. 7, the Raman spectroscopy apparatus 100 includes the aforementioned optical field enhancement substrate 1, an excitation light projection section 140 for projecting excitation light L1 onto the optical field enhancement substrate 1, and a light detection section 150 for detecting Raman scattered light L2 emitted from a subject S and enhanced by the action of the optical field enhancement substrate.

The excitation light projecting section 140 includes a semiconductor laser 141 that emits the excitation light L1, a mirror 142 that reflects the light L1 emitted from the semiconductor laser 141 toward the substrate 1, a half-mirror 144 that transmits the excitation light L1 reflected from the mirror 142 and reflects light from the substrate 1, which includes Raman scattered light L2 generated from the subject S by receiving the excitation light L1 and enhanced, toward the light detection section 150, and a lens 146 that focuses the excitation light L1 transmitted through the half mirror 144 on an area of the optical field enhancement substrate 1 on which the subject S is placed.

The light detection section 150 includes a notch filter 151 that absorbs the excitation light L1 included in the light reflected from the half mirror 144 and transmits light other than the excitation light, a pin-hole plate 153 having a pinhole 152 for removing noise light, a lens 154 that focuses the enhanced Raman scattered light L2 emitted from the subject S and transmitted through the lens 146 and the notch filter 151 on the pin-hole 152, a lens 156 that collimates the Raman scattered light passed through the pin-hole 152, and a spectroscope 158 that detects the enhanced Raman scattered light.

A Raman spectroscopy method for measuring a Raman spectrum of the subject S using the aforementioned Raman spectroscopy apparatus 100 will be described.

The excitation light L1 is emitted from the semiconductor laser 141 of the light projection section 140, reflected by the mirror 142 toward the substrate 1, transmitted through the half mirror 144, focused by the lens 146, and projected onto the optical field enhancement substrate 1.

The projection of the excitation light L1 onto the optical field enhancement substrate 1 causes localized plasmon resonance to be induced in the fine uneven metal structure, and enhanced optical field is created on the surface of the metal film 24. Raman scattered light L2 emitted from the subject S and enhanced by the enhanced optical field is transmitted through the lens 146, reflected by the half mirror 144 toward the spectroscope 158. Here, the excitation light L1 reflected from the optical field enhancement substrate 1 is reflected by the half mirror 144 toward the spectroscope 158, but it is cut by the notch filter 151. In the mean time, light having a wavelength different from that of the excitation light is transmitted through the notch filter 151, focused by the lens 154, passed through the pin-hole 152, collimated again by the lens 156, and incident on the spectroscope 158. In the Raman spectroscopy apparatus, Rayleigh scattered light (or Mie scattered light) has the same wavelength as that of the excitation light L1 so that it is cut by the notch filter 151 and never incident on the spectroscope 158. The Raman scattered light L2 is incident on the spectroscope 158 and Raman spectrum measurement is performed.

The Raman spectroscopy apparatus 100 of the present embodiment is configured using the optical field enhancement substrate 1 of the embodiment described above and Raman enhancement takes place effectively so that highly accurate Raman spectroscopy measurement with high data reliability and reproducibility can be conducted. As the uneven structure on the surface of the optical field enhancement substrate 1 has high in-plane uniformity, reproducible data may be obtained even when the measurement is repeated with respect to the same sample by changing the position where the light is projected. It is, therefore, possible to increase the reliability of data by obtaining a plurality of data with respect to the same sample by changing the position where the light is projected.

Adoption of a configuration in which detection is performed from the back surface side of the optical field enhancement substrate 1, as in the Raman spectroscopy apparatus 100 of the present embodiment, allows the enhanced Raman scattered light that occurs most strongly at the interface between the metal film and subject to be detected from the back surface side of the transparent substrate without being blocked by the subject even when the subject is a large sample like a cell. The present inventors have confirmed that enhanced Raman scattered light can be detected from the back surface side of the transparent substrate without being affected by the metal film (Example to be described later).

Figure 8:
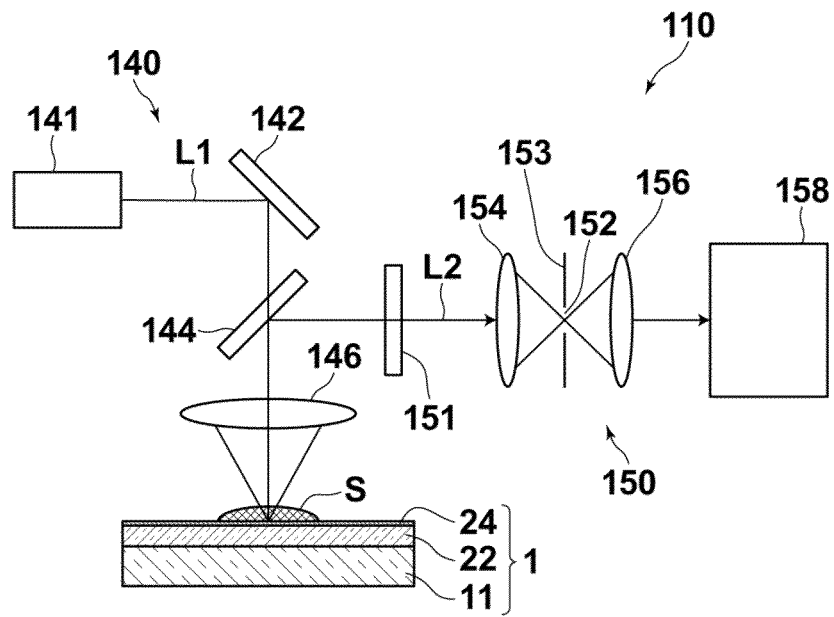
FIG. 8 is a schematic diagram of a design change example of the enhanced Raman spectroscopy apparatus.

The Raman spectroscopy apparatus 100 of the aforementioned embodiment is configured such that the excitation light is incident on the optical field enhancement device 1 from the side (back surface of the device) opposite to the sample holding surface (front surface) and Raman scattered light is detected also from the back surface side, but the apparatus may be configured such that the excitation light L1 is incident from the front surface side (sample holding surface) of the metal film 24 and Raman scattered light L2 is detected also from the front surface side as in a conventional apparatus and as a Raman spectroscopy apparatus 110 of a design change example shown in FIG. 8.

Further, a configuration may be adopted in which either the excitation light projection section or light detection section is disposed on the front surface side of the metal film 24 and the other is disposed on the back surface side of the substrate 1.

As described above, since the optical field enhancement device of the present invention uses a transparent substrate, light may be projected either from the front surface side of the metal film or from the back surface side of the transparent substrate, and light generated from the sample by the projected light is also detected from either the front surface side of the metal film or from the back surface side of the transparent substrate. Thus, the projection of excitation light and detection of detection light may be performed either from the front surface side of the metal film or from the back surface side of the transparent substrate according to the type, size, and the like of the subject. This provides a high degree of flexibility in measurement and allows detection with an improved signal-to-noise ratio.

Figure 9:
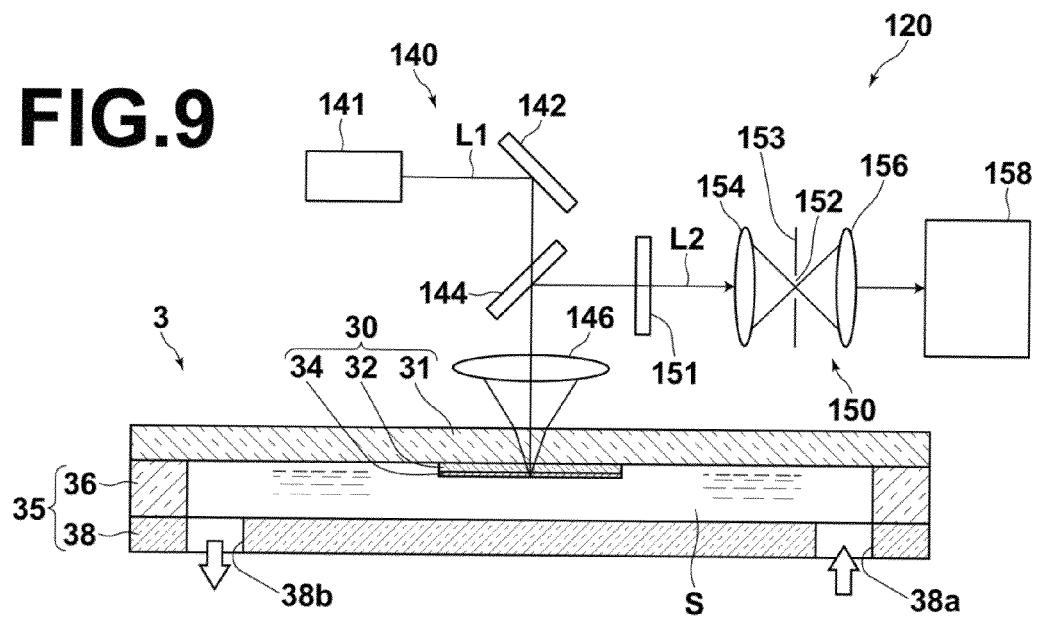
FIG. 9 is a schematic diagram of an enhanced Raman spectroscopy apparatus having the optical field enhancement sample cell 3, illustrating the configuration thereof.

FIG. 9 is a schematic diagram of a Raman spectroscopy apparatus 120 having a flow cell, which is the optical field enhancement device 3 of the third embodiment described above.

The Raman spectroscopy apparatus 120 shown in FIG. 9 differs from the Raman spectroscopy apparatus 100 shown in FIG. 7 in that it includes a flow cell type optical field enhancement sample cell 3 instead of the optical field enhancement substrate 1. Provision of such flow cell type optical field enhancement device allows Raman spectrum to be measured while a liquid sample, as the subject, is flowing down.

In the measurement by the flow cell type device 3, a configuration may be adopted in which the excitation light is inputted from the front surface side of the metal film and Raman scattered light is detected from the front surface side of the metal film. But, when measuring Raman scattered light while a liquid sample is flowing down, the transmittance and absorptance of the liquid sample with respect to the Raman scattered light may vary with the movement of the liquid sample, so that a configuration in which Raman scattered light is detected from the back surface side of the substrate 30 is preferable, as illustrated in FIG. 9.

As described above, the optical field enhancement device may be applied to a plasmon enhancement fluorescence detection apparatus. In this case also, a subject is placed on the metal film of the optical field enhancement device, and excitation light may be inputted from the subject side and enhanced fluorescence may be detected from the subject side, or excitation light may be inputted from the back surface side of the transparent substrate and fluorescence may be detected from the back surface side. Otherwise, a configuration may be adopted in which excitation light is projected from the subject side and fluorescence is detected from the back surface side of the transparent substrate.

EXAMPLE

Hereinafter, a specific example of an optical field enhancement substrate 1, the first embodiment of the optical field enhancement device of the present invention, and Raman spectroscopy measurement results using a measuring sample will be described.

[Manufacturing Method of Optical Field Enhancement Substrate]

A glass substrate (BK-7, Corning Eagle 2000) was used as the transparent substrate body 11. Then, the substrate was cleaned by ultrasonic cleaning (45 kHz, three minutes) with pure water. Aluminum 20 was layered on the cleaned glass substrate 11 with a thickness of 50 nm using a sputtering system (CANON ANELVA Corporation). The thickness of the aluminum was measured using a profilometer (TENCOR Corporation) and verified to be 50 nm (±10%).

Thereafter, a container containing pure water was placed on a hot plate to boil the pure water. The glass substrate 11 with the aluminum 20 was immersed in the boiling water and taken out after five minutes. Here, it was confirmed that the aluminum turned to transparent about one or two minutes after it was immersed in the boiling water. This boil treatment (boehmite treatment) turned the aluminum 20 to the boehmite layer 22. The observation result of the surface of the boehmite layer 22 using a SEM (Hitachi, S4100) has already been shown in FIG. 3. Finally, Au was deposited on the boehmite layer 22 with a thickness of 40 nm as the metal film 24.

[Raman Scattered Light Measurement]

Using a dye (Rhodamine 6G)-attached measuring sample, as a subject, on the optical field enhancement substrate manufactured in the manner described above, Raman scattered light was measured from the front and back surface sides of the substrate.

(Method of Producing Measuring Sample)

A method of producing the measuring sample will be described with reference to FIG. 10.

An optical field enhancement substrate produced by placing a mask on a peripheral portion of a transparent substrate when the metal film was formed on the transparent fine uneven structure layer by vapor deposition and removing the mask after the deposition in the method of manufacturing the optical field enhancement substrate 1 was used. Thus, the metal film was not formed on the masked area of the measuring sample optical field enhancement substrate.

Figure 10:
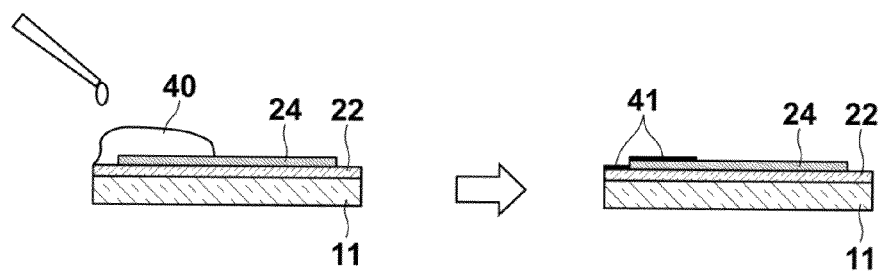
FIG. 10 shows schematic cross-sectional views of a measuring sample in an Example, illustrating the manufacturing steps thereof.

First, a solution (R6G/ethanol: 10 mM) 40 which includes a dye (Rhodamine 6G) was dropped on an area where the gold film 24 was formed and an area where it was not formed, as illustrated in the drawing on the left of FIG. 10. Then, by drying the droplet, a measuring sample in which the dye 41 was fixed on both of the areas with and without the metal film 24 was obtained, as illustrated in the drawing on the right of FIG. 10.

(Raman Scattered Light Measurement Method)

Figure 11:
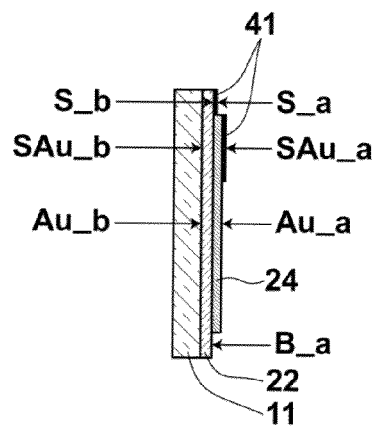
FIG. 11 illustrates positions of the measuring sample for measuring Raman scattered light.

Excitation light was projected onto seven measuring points of the measuring sample illustrated in FIG. 11, namely, front surface side of boehmite B_a, front surface side of gold film Au_a, back surface side of gold film Au_b, front surface side of the dye on the gold film SAu_a, back surface side of the dye on the gold film SAu_b, front surface side of the dye on the boehmite S_a, and back surface side of the dye on the boehmite S_b, and Raman scattered light was measured.

Raman scattered light was detected using a microscopic Raman spectroscopy apparatus (Raman 5). For example, the measurement of the front surface side of the dye on the metal film is a measurement in which the excitation light was projected from the front surface side of the dye on the metal film and Raman scattered light was detected from the front surface side of the dye on the metal film. As for the excitation light, laser light with a peak wavelength of 785 nm was used and observation was performed with a magnification of 20.

(Measurement Results)

Figure 12:
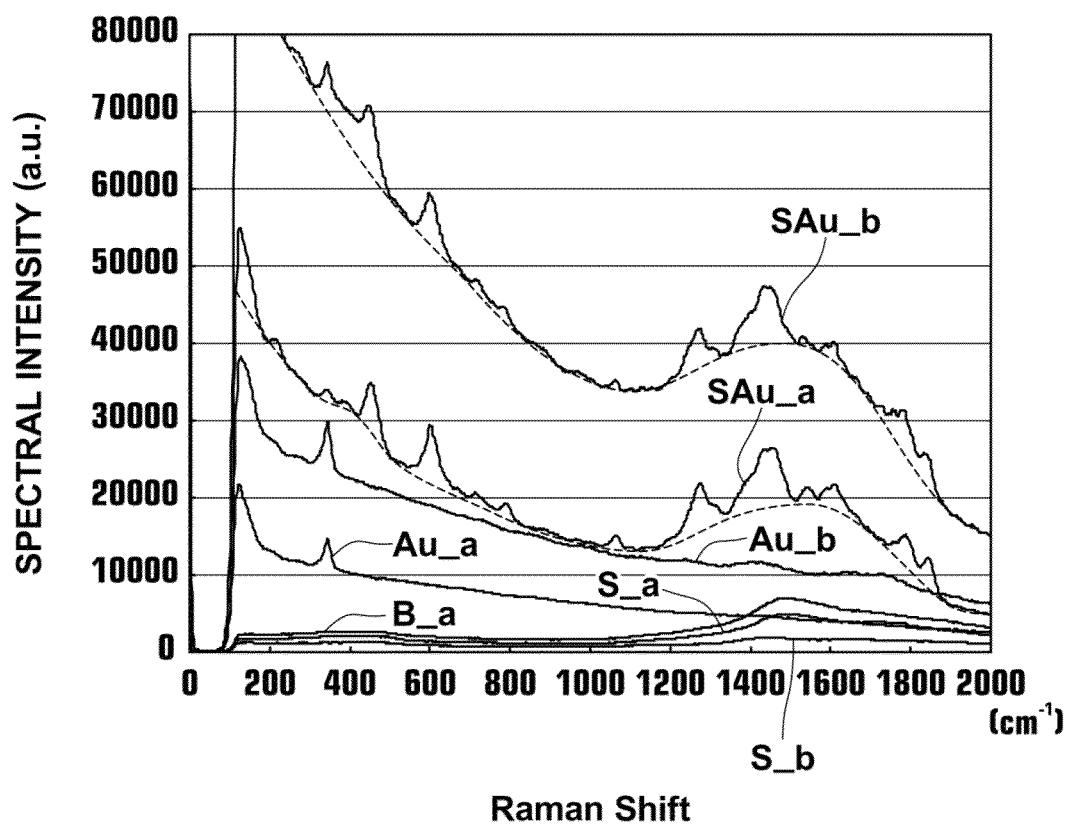
FIG. 12 is a graph illustrating a Raman shift spectrum distribution obtained from the measuring sample.

FIG. 12 is a graph illustrating a Raman shift spectrum distribution from each position detected by the microscopic Raman spectroscopy apparatus.

Virtually no signal of Raman scattered light was detected from the front surface side of boehmite B_a, front surface side of the dye fixed on the boehmite S_a, and back surface side of the dye on the boehmite S_b. As described above, it is known that the signal at a position where the gold film was not provided is very low measured from the front surface side or from the back surface side.

With respect to the position where the dye was fixed on the gold film, high intensity spectrum was obtain in each detection from the front surface side SAu_a and back surface side SAu_b but with a high background. In FIG. 12, portions that can be regarded as backgrounds are indicated by the dashed lines. Signals obtained by subtracting the backgrounds can be pure Raman shift signals. Raman shift signals detected at the corresponding positions between detection from the front surface side and back surface side of the dye on the gold film SAu_a and SAu_b were identical in intensity.

Heretofore, there has been no case in Raman measurement in which a Raman signal is detected from the back surface side of the substrate, and present inventors have found out that a Raman signal can be detected from the back surface side of the substrate through the aforementioned Raman measurement using the optical field enhancement device of the present invention.

From the measurement results; the present inventors assume that an optical field enhanced by localized plasmon created by the light projected onto the fine uneven metal structure interacts with the sample and further a some sort of interaction between the fine uneven metal structure and Raman scattered light allowed a signal to be obtained from the back surface side which is comparable in intensity to that obtained from the front surface side.

In the present Example, a dried and fixed dye was used as the subject in the measuring sample, that is, the thickness of the subject was very thin so that the signals between the front surface side and back surface side of the dye on the gold film were almost identical in intensity. In the case where Raman spectroscopy is performed for a sample having a thickness in the order of one micrometer, such as a cell, however, it can be more advantageous to detect a signal near the interface between the gold film having a high enhancement effect and sample from the back surface side.

Such Raman signal detection from the back surface side of the substrate has been achieved for the first time by the optical field enhancement device of the present invention having a transparent substrate body and a fine uneven structure. It is difficult for a conventional optical field enhancement substrate configured such that an uneven structure is provided on an opaque substrate or an uneven structure made of an opaque material is provided on a transparent substrate to detect Raman scattered light from the back surface side of the substrate.

Heretofore, as it has not been considered that Raman light enhanced by an enhanced optical field created in the surface of an uneven metal structure can be detected from the back surface side of the substrate, the idea itself of fabricating the substrate and uneven structure with a transparent material has not existed in the first place and there has been no enhanced Raman device (optical field enhancement substrate) in which both of the substrate body and fine uneven structure are made of a transparent material.

As described above, the optical field enhancement device of the present invention includes a transparent substrate having an uneven structure on a surface and a metal film formed on the substrate. The device is very useful as it allows signal light to be detected not only from the metal film side of the transparent substrate but also from the back surface side of the substrate.

What is claimed is:

1. An optical field enhancement device, comprising a transparent substrate having a transparent fine uneven structure on a surface and a metal film formed on a surface of the transparent fine uneven structure on the surface of the substrate, wherein the device is configured such that an enhanced optical field is created on a surface of the metal film by an optical field enhancement effect of localized plasmon induced on the surface of the metal film by light projected onto the fine uneven structure on which the metal film is formed.

2. The optical field enhancement device of claim 1, wherein the transparent substrate is formed of a transparent substrate body and a fine uneven structure layer provided on a surface of the transparent substrate body, wherein the layer is made of a material different from that of the transparent substrate body and constitutes the fine uneven structure.

3. The optical field enhancement device of claim 2, wherein the fine uneven structure layer is made of boehmite.

4. The optical field enhancement device of claim 1, wherein the metal film has a thickness of 10 to 100 nm.

5. The optical field enhancement device of claim 1, wherein the device comprises a transparent second fine uneven structure acting as an antireflection film on a back surface of the transparent substrate.

6. The optical field enhancement device of claim 5, wherein the second fine uneven structure is formed of a fine uneven structure layer made of boehmite.

7. The optical field enhancement device of claim 1, wherein the device comprises a liquid sample holding member for holding a liquid sample on the metal film of the transparent substrate.

8. The optical field enhancement device of claim 7, wherein the liquid sample holding member has an inlet section and an outlet section for a liquid.

* * * * *